United States Patent [19]

Tou et al.

[11] 4,442,298

[45] Apr. 10, 1984

[54] CHEMICAL SYNTHESIS OF ETHYLENE/MALEIC ANHYDRIDE DIMER WITH PHENYLETHYL END GROUP

[75] Inventors: Jacob S. Tou; Alfred A. Schleppnik, both of St. Louis, Mo.

[73] Assignee: Monsanto Company, St. Louis, Mo.

[21] Appl. No.: 413,009

[22] Filed: Aug. 30, 1982

[51] Int. Cl.$^3$ ............................................ C07D 307/60
[52] U.S. Cl. .................................. 549/252; 260/465 D
[58] Field of Search ........................................ 549/252

[56] References Cited

U.S. PATENT DOCUMENTS

| 2,913,437 | 11/1959 | Johnson | 260/78.5 |
| 2,957,767 | 10/1960 | Williams | 96/114 |
| 4,255,537 | 3/1981 | Fields et al. | 525/328 |
| 4,309,413 | 1/1982 | Fields et al. | 424/78 |

OTHER PUBLICATIONS

Hodnett and Tien Hai Tai, *J. Med. Chem.* 17 (12), 1335–1337 (1974).

Fields et al., *J. Med. Chem.* 25 (9), 1060–1064 (1982).

*Primary Examiner*—Henry R. Jiles
*Assistant Examiner*—Bernard Dentz
*Attorney, Agent, or Firm*—Scott J. Meyer; James W. Williams, Jr.

[57] ABSTRACT

A phenylethyl substituted dimer of ethylene and maleic anhydride, names 7-phenyloctane-(1,2),(5,6)-dianhydride, is chemically synthesized by
  (a) alkylating alkyl 2,4-dihalobutyrate with alkyl 2-cyano-3-phenylbutyrate,
  (b) alkylating the resulting halide condensation product with a carboxylate selected from the group consisting of trialkyl ethane-1,1,2-tricarboxylate and dimethyl cyanoethane-1,2-dicarboxylate,
  (c) acid hydrolyzing the resulting tetra or pentaester accompanied by decarboxylating, and
  (d) dehydrating the resulting tetra-acid to yield the desired phenylethyl substituted dimer of ethylene and maleic anhydride,
wherein the alkyls in the butyrate and carboxylate ester groups each contain from one to about four carbon atoms and halo is selected from the group consisting of bromo, chloro and iodo.

The dimer has anti-tumor and anti-viral properties and can be used in silver halide emulsions.

6 Claims, No Drawings

CHEMICAL SYNTHESIS OF ETHYLENE/MALEIC ANHYDRIDE DIMER WITH PHENYLETHYL END GROUP

BACKGROUND OF THE INVENTION

This invention relates to a phenylethyl substituted dimer of ethylene and maleic anhydride and to a method for its complete chemical synthesis without polymerization. This dimer is appropriately named 7-phenyloctane-(1,2),(5,6)-dianhydride.

It is well-known that various polyanionic compounds such as polyacrylic acid, pyran copolymer (divinylether/maleic anhydride) and ethylene/maleic anhydride copolymer (EMA) have antitumor, antiviral and other pharmacological and biological properties. For example, polyanions having the following structural units have been found active against both the solid (intravascular) and ascitic (intraperitoneal) forms of the Walker carcinoma 256 of the rat as determined by the National Cancer Institute:

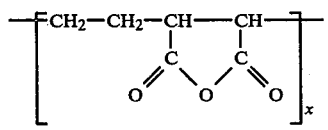

See, for example, Hodnett and Tien Hai Tai, J. Med. Chem. 17 (12), 1335–1337 (1974). The ethylene and succinyl moieties in the above polymeric structure are linked together by the polymerization of ethylene and maleic anhydride.

More recently, it has been shown that certain ammoniated derivatives of such ethylene/maleic anhydride polymers having relatively low molecular weight have enhanced antitumor and immunological activity. See U.S. Pat. Nos. 4,255,537 and 4,309,413. The average molecular weight of these improved polymers ranges from about 300 to about 1500. The smallest component of these polymeric substances having a molecular weight of about 300 is essentially a dimer of ethylene and maleic anhydride.

The previously disclosed method of making the foregoing ethylene/maleic anhydride polymeric compounds of low molecular weight comprises the polymerization of ethylene and maleic anhydride in the presence of alkylated aromatic hydrocarbon having at least one α-hydrogen. Ethyl benzene is especially preferred. The use of ethyl benzene in the reaction medium results in the introduction of a phenylethyl end group in the polymeric structure. Such end group constitutes a relatively high percentage of the total structure for a polymer of relatively low molecular weight of about 300. The structure of these relatively low molecular weight polymers of ethylene and maleic anhydride having the phenylethyl end group can be represented as follows:

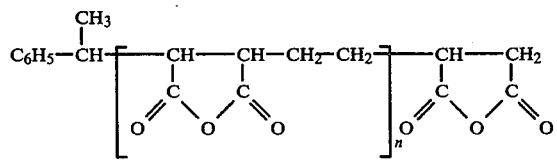

See FIG. 1 in Fields et al, J. Med. Chem. 25(9), 1060–1064 (1982), for a report of the above structure. When n in the above formula is equal to one, the polymer would be a phenylethyl substituted dimer having a succinyl anhydride terminal group and a molecular weight of 330.

The EMA type copolymers, including dimers, and their ammoniated derivatives, are also known to be suitable for various non-pharmaceutical uses. Illustrative of such uses is the silver halide dispersion disclosed in U.S. Pat. 2,957,767. Other non-pharmaceutical uses of low molecular weight EMA polymers prepared in ethyl benzene solvent are described, for example, in U.S. Pat. No. 2,913,437.

DESCRIPTION OF THE INVENTION

In accordance with the present invention, a phenylethyl substituted dimer of ethylene and maleic anhydride is prepared completely by chemical synthesis without polymerization.

In general, the method of the present invention comprises:

(a) alkylating alkyl 2,4-dihalobutyrate with alkyl 2-cyano-3-phenylbutyrate, (b) alkylating the resulting halide condensation product with a carboxylate selected from the group consisting of trialky ethane-1,1,2-tricarboxylate and dimethyl cyanoethane-1,2-dicarboxylate, (c) acid hydrolyzing the resulting tetra or pentaester accompanied by decarboxylating, and (d) dehydrating the resulting tetra-acid to yield the desired phenylethyl substituted dimer of ethylene and maleic anhydride, wherein the alkyls in the butyrate and carboxylate ester groups each contain from one to about four carbon atoms and halo is selected from the group consisting of bromo, chloro and iodo.

The product made by the aforesaid method is conveniently described herein as a phenylethyl substituted dimer of ethylene and maleic anhydride in view of conventional polymer nomenclature used heretofore to describe substances of this type. This product also can be appropriately named 7-phenyloctane-(1,2),(5,6)dianhydride based on its chemical structure.

In the method of the present invention, the stated alkyls in the butyrate and carboxylate ester groups are preferably methyl and the stated halo substituents preferably are bromo.

The aforesaid stepwise production of the desired dimer can be illustrated by the following reaction equations in which the preferred methyl ester groups and bromo substituents are employed in the reactants and in which the carboxylate reactant is trimethyl ethane-1,1,2-tricarboxylate. It will be appreciated that, alternatively, the alkyls in the butyrate and carboxylate ester groups can be, for example, ethyl, propyl or butyl, the halo substituents can be chloro or iodo, and the carboxylate reactant can be dialkyl cyanoethane-1,2-dicarboxylate with substantially similar results as in the preferred reaction sequence.

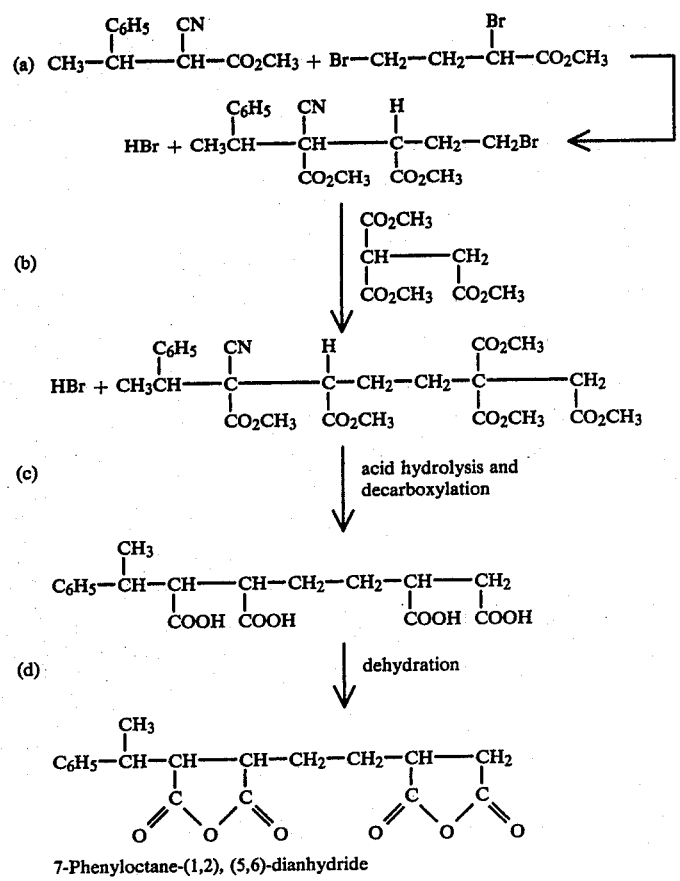

7-Phenyloctane-(1,2), (5,6)-dianhydride

The initial reactants for step (a) in the preferred reaction sequence can be prepared by conventional procedures. Thus, the starting methyl 2-cyano-3-phenylbutyrate can be prepared by a Knoevenagel type condensation of acetophenone and cyanoacetate followed by hydrogenation of the resulting unsaturated Knoevenagel adduct. The Knoevenagel type condensation reaction of ketone with active methylene compounds was first reported by Knoevenagel, Ber. 31, 2596 (1898).

The starting methyl 2,4-dibromobutyrate can be prepared by bromination of butyrolactone with phosphorus tribromide and bromine at 100°-120° C. followed by acid hydrolysis, e.g. with hydrochloric acid, in methanol and removal of the hydrogen halides and phosphate esters. Preparation of methyl 2,4-dibromobutyrate by this general reaction is known from Wladislaw, J. Org. Chem. 26, 711-713 (1961). Halogenation of γ-butyrolactone to yield α,γ-dibromobutyric acid or α,γ-dichlorobutyric acid was earlier described by Livak et al., J. Amer. Chem. Soc. 67, 2218-20 (1945) and in U.S. Pat. Nos. 2,530,348 and 2,557,779. However, in order to prevent elimination of hydrogen halide which would lead to the formation of α-halo-γ-butyrolactone, the crude reaction product is converted immediately into the corresponding ester.

The trimethyl ethane-1,1,2-tricarboxylate reactant which can be used in step (b) also is a known compound which was first described by C. A. Bischoff, Ber. 29 (1), 966-967 (1896). It can be prepared by reaction of methyl chloroacetate and dimethyl malonate in the presence of sodium methoxide in methanol solvent.

The dimethyl cyanoethane-1,2-dicarboxylate reactant, which similarly can be used in step (b), can be prepared by the reaction of methyl cyanoacetate and methyl chloroacetate in the presence of potassium carbonate in dimethylformamide solvent by procedures analogous to the method for alkylation of methyl 2-cyanopropionate described by D. A. White, Synthetic Comm. 7(8), 559-568 (1977).

The alkylation reaction in steps (a) and (b) also are each preferably carried out in the presence of potassium carbonate in organic solvent medium such as, e.g., dimethylformamide (DMF) or dimethylsulfoxide (DMSO) solvent, in a manner analogous to the above cited method for alkylation of methyl 2-cyanopropionate.

The acid hydrolysis and decarboxylation in step (c) is conveniently carried out with acid such as hydrochloric acid, preferably in about a 1:1 solvent mixture of water and acetic acid at refluxing temperature conditions.

The final step (d) of the synthesis which comprises dehydration of the tetra-acid is preferably carried out by reaction with acetyl chloride in boiling acetic anhydride. The desired dimer is thus obtained as a colored glassy solid. Overall yields using the aforesaid preferred process, including the Knoevenagel condensation reaction as an initial starting point, have been in the range of 10-17% based on acetophenone.

The final phenylethyl substituted dimer of ethylene and maleic anhydride is a useful intermediate which can be reacted with ammonia to produce ammoniated derivatives of the type described in the aforesaid U.S. Pat. Nos. 4,255,537 and 4,309,413 and Fields et al., J. Med. Chem. 25(9), 1060-1064 (1982). The dimer product is also suitable for various non-pharmaceutical users such as described in U.S. Pat. Nos. 2,957,767 and 2,913,437.

In the aforesaid stepwise process, it will be appreciated that the alkylation reactions can be conducted in the presence of basic reagents other than potassium carbonate. Thus, sodium hydride and sodium methoxide can be used in the alkylation reactions. So also, other acid media such as, for example, sulfuric acid can be used for the hydrolysis step. The dehydration step alternatively can be carried out by refluxing in reagents such as p-toluenesulfonic acid in toluene or benzene solvent and collecting the water in a Dean Stark trap.

The following detailed examples will further illustrate the invention although it will be understood that the invention is not limited to these specific examples.

In steps (a) and (b) of the method of the present invention as illustrated in the preferred reaction sequence, above, and in Examples 3, 4 and 7 below, the following novel intermediate carboxylate compounds are prepared:

Dimethyl 2-phenyl-3-cyano-6-bromohexane-3,4-dicarboxylate;
Pentamethyl 6-cyano-7-phenyloctane-1,2,2,5,6-pentacarboxylate; and
Tetramethyl 2,6-dicyano-7-phenyloctane-1,2,5,6-tetracarboxylate.

EXAMPLE 1

Methyl 2-cyano-3-phenylbutyrate

A mixture of methyl cyanoacetate (198 g, 2.0 moles), acetophenone (240 g, 2.0 moles), ammonium acetate (30.8 g, 0.4 moles) and acetic acid (96 g, 1.60 moles) in toluene was refluxed with a Dean and Stark trap until water separation ceased (about 4 hours). The resulting Knoevenagel adduct was cooled and stirred under hydrogen (60 psig) with 5% palladium on carbon (8 g) for 2 days. The solution was then depressurized, degassed, filtered and evaporated. The liquid residue was distilled and the fraction with bp 110°-140° C. (about 0.03 mm) collected as mixed stereoisomers of methyl 2-cyano-3-phenylbutyrate as identified by the nmr spectrum.

EXAMPLE 2

Methyl 2,4-dibromobutyrate

A 3 liter round bottom flask equipped with a thermometer, subsurface additional funnel, condenser vented to a scrubber and mechanical stirrer was charged with butyrolactone (600 g; 6.98 moles) and phosphorus tribromide (12 ml). Subsurface addition of bromine was initiated. Heat was evolved and the rate was maintained at that necessary to keep the reaction mixture at about 110° C. After 7½ hours, 1166 g (7.29 moles) of bromine had been added and the color of bromine persisted in the reaction mixture. Over the course of a further two days, repeated additions of phosphorus tribromide, which accelerated the rate of bromine consumption and of bromine, were made at 100°-120°. Accordingly, 1636 g (10.2 moles, 1.46 moles/mole butyrolactone) phosphorus tribromide were added during the reaction period.

The cooled (<5°) reaction mixture was treated with methanol (2.5 liters), while cooling in an ice-water bath. The mixture was saturated with hydrogen chloride and allowed to stand at room temperature overnight. The solution was stripped of hydrogen halides and methanol leaving a two phase residue. The larger lower phase was separated and distilled (the upper layer appeared to be mainly phosphorus esters and was discarded). Two fractions were collected having bp 69°-72° (0.7-0.8 mm) (951 g) and bp 72°-9° (1.0 to 1.1 mm) (434 g). These fractions were washed with 3% aqueous sodium bicarbonate to remove phosphate esters and dried on a rotary evaporator, to give 944 g and 426 g of methyl 2,4-dibromobutyrate product of 97% and 92% purity, respectively.

EXAMPLE 3

Dimethyl 2-phenyl-3-cyano-6-bromohexane-3,4-dicarboxylate

A mixture of methyl 2-cyano-3-phenylbutyrate (78 g, 0.37 mole), methyl 2,4-dibromobutyrate (122 g, 0.47 mole), potassium carbonate (65 g, 0.47 mole) and DMSO (50 ml) was stirred on a ball mill apparatus. The reaction was completed in four hours. Ice water was added and the mixture was neutralized by adding cold hydrochloric acid. The aqueous solution was extracted several times with ether. The combined organic solution was washed sequentially with cold aqueous sodium bicarbonate and brine, then dried over magnesium sulfate. After removal of the solvent, the residue was purified by Kugelrohr distillation (100° C., 30 microns) to remove low boiling materials. The remaining oily residue (118 g., 84%) was found to be mainly the title bromide condensation product ($\mu$<95% GC purity). MS m/e (% relative intensity) 383(M.+, 3) 381 (3), 202 (33), 182 (7), 180 (7), 105 (100).

EXAMPLE 4

Pentamethyl 6-cyano-7-phenyloctane-1,2,2,5,6-pentacarboxylate

A mixture of the bromide condensation product of Example 3 (118 g, 0.3 mole), trimethyl ethane-1,1,2-tricarboxylate (84 g, 0.41 mole), potassium carbonate (62 g, 0.45 mole) and DMSO (50 ml) was ball-milled for about four days. GLPC indicated that the bromide reactant had been totally consumed. Workup similar to that described above in Example 3 gave a colored oil. The low-boiling impurities were removed via Kugelrohr (110° C., 20 microns) to give 120 g of the title pentaester.

MS M/e (% relative intensity): 501 (M.+,1), 474 (3), 304 (12), 204 (9), 202 (10), 105 (100).

EXAMPLE 5

7-Phenyloctane-1,2,5,6-tetracarboxylic acid

A mixture of the pentaester product of Example 4 (120 g, 0.24 mole), concentrated hydrochloric acid (200 ml), water (200 ml) and acetic acid (200 ml) was refluxed for four days. The cloudy solution turned clear after about 48 hours. Removal of solvents in vacuo gave a glass-like material which was then dissolved in acetone and was stirred overnight. The salt (ammonium chloride) was removed by filtration and the remaining solution was condensed to afford 80 g of the glassy title tetra-acid product which was used in the sequential reaction of Example 6 without further purification. MS m/e (% relative intensity) 349 (CI, M.+ +1—H$_2$O),330 (M.+—2 H$_2$O,1), 303 (2), 284 (5), 105 (100).

EXAMPLE 6

7-Phenyloctane-(1,2),(5,6)-dianhydride

The crude tetra-acid product of Example 5 (~70 g), acetyl chloride (60 ml) and acetic anhydride (150 ml)

were stirred and refluxed for 24 hours. The solution was then concentrated to give a dark oily residue. This material was percolated in methylene chloride through a charcoal/silica gel column. The collected mixture was stripped of solvent and the low-boiling impurity was removed via Kugelrohr (120° C., 100 microns) to afford 61 g of thick oil which solidified upon standing at room temperature. This crude glassy solid of the title dianhydride product displayed the following properties:

IR (CDCl$_3$). 2950, 1850, 1780, 1600 cm$^{-2}$; $^1$H NMR (CDCl$_3$) δppm 7.3 (S, phenyl-H), 1.2–4.0 (broad); MS m/e (% relative intensity) 331 (CI, M.++1) 330 (M.+,3), 302 (6), 284 (16), 145 (25), 105 (100). C-13 NMR (CHCl$_3$)δppm for downfield absorptions: 173, 172, 171, 169 (anhydride carbonyl), 140, 129, 128, 127 (aromatic carbons).

EXAMPLE 7

Tetramethyl 2,6-dicyano-7-phenyloctane-1,2,5,6-tetracarboxylate

In a manner similar to the procedure of Example 4, dimethyl cyanoethane-1,2-dicarboxylate was condensed with the bromide product of Example 3 to give the title tetraester. MS M/e (% relative intensity): 473 (CI, M++1), 441 (2), 239 (12), 202 (13), 105 (100).

The tetraester prepared in Example 7 can be used in place of an equivalent amount of the pentaester of Example 5 followed by substantially similar acid hydrolysis and decarboxylation to produce the tetracarboxylic acid of Example 5.

Ethyl 2-cyano-3-phenylbutyrate and ethyl 2,4-dichlorbutyrate can be used in place of methyl 2-cyano-3-phenylbutyrate and methyl 2,4-dibromobutyrate, respectively, in the alkylation reaction of Example 3 to produce the corresponding diethyl 2-phenyl-3-cyano-6-chlorohexane-3,4-dicarboxylate. The latter product can then be reacted with the tricarboxylate of Example 4 and the dicarboxylate of Example 7 to give the corresponding pentaester and tetraester products.

In the foregoing Examples,
IR = Infrared Spectra,
NMR = Nuclear Magnetic Resonance Spectra, and
MS = Mass Spectra.

Various other examples will be apparent to the person skilled in the art after reading the present disclosure without departing from the spirit and scope of the invention and it is intended that all such further examples be included within the scope of the invention.

What is claimed is:

1. A method for the chemical synthesis of a phenylethyl substituted dimer of ethylene and maleic anhydride comprising
   (a) alkylating alkyl 2,4-dihalobutyrate with alkyl 2-cyano-3-phenylbutyrate,
   (b) alkylating the resulting halide condensation product with a carboxylate selected from the group consisting of trialkyl ethane-1,1,2-tricarboxylate and dimethyl cyanoethane-1,2-dicarboxylate,
   (c) acid hydrolyzing the resulting tetra or pentaester accompanied by decarboxylating, and
   (d) dehydrating the resulting tetra-acid to yield the desired phenylethyl substituted dimer of ethylene and maleic anhydride,
   wherein the alkyls in the butyrate and carboxylate ester groups each contain from one to about four carbon atoms and halo is selected from the group consisting of bromo, chloro and iodo.

2. The method of claim 1 in which the alkyls in the butyrate and carboxylate ester groups are methyl, the halo substituents are bromo and the carboxylate is trimethyl ethane-1,1,2-tricarboxylate.

3. The method of claim 2 in which the alkylating steps (a) and (b) are carried out in the presence of potassium carbonate and organic solvent medium selected from the group consisting of DMF and DMSO.

4. The method of claim 2 in which the acid hydrolyzing and decarboxylating step (c) is carried out with hydrochloric acid in about a 1:1 solvent mixture of water and acetic acid at refluxing temperature.

5. The method of claim 2 in which the dehydrating step (d) is carried out by reaction of the tetra-acid with acetyl chloride in boiling acetic anhydride.

6. The method of claim 2 in which the alkylating steps (a) and (b) are carried out in the presence of potassium carbonate and organic solvent medium selected from the group consisting of DMF and DMSO, the acid hydrolyzing and decarboxylating step (c) is carried out with hydrochloric acid in about a 1:1 solvent mixture of water and acetic acid at refluxing temperature, and in which the dehydrating step (d) is carried out by reaction of the tetra-acid with acetyl chloride in boiling acetic anhydride.

* * * * *

UNITED STATES PATENT AND TRADEMARK OFFICE
CERTIFICATE OF CORRECTION

PATENT NO. : 4,442,298

DATED : April 10, 1984

INVENTOR(S) : Jacob S. Tou and Alfred A. Schleppnik

It is certified that error appears in the above—identified patent and that said Letters Patent is hereby corrected as shown below:

Column 3, in the product of step (a), that portion of the formula reading

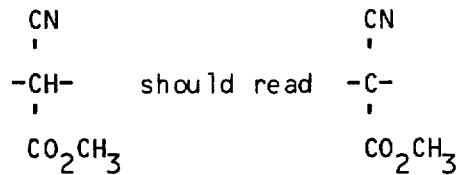

Signed and Sealed this

Twenty-first Day of May 1985

[SEAL]

Attest:

DONALD J. QUIGG

Attesting Officer     Acting Commissioner of Patents and Trademarks